US005493894A

United States Patent [19]
Dailey et al.

[11] Patent Number: 5,493,894
[45] Date of Patent: Feb. 27, 1996

[54] SYSTEM AND METHOD FOR IMPACT TESTING WEDGE TIGHTNESS IN AN ELECTRICAL GENERATOR

[75] Inventors: George F. Dailey; Mark W. Fischer; Harry L. Sill, all of Pittsburgh, Pa.

[73] Assignee: Westinghouse Electric Corporation, Pittsburgh, Pa.

[21] Appl. No.: 418,358

[22] Filed: Apr. 7, 1995

[51] Int. Cl.$^6$ .................................................. G01N 3/00
[52] U.S. Cl. .............................. 73/12.09; 73/865.8
[58] Field of Search .......................... 73/12.09, 12.12, 73/865.8; 33/656; 324/207.18

[56] References Cited

U.S. PATENT DOCUMENTS

| | | | |
|---|---|---|---|
| 4,962,660 | 10/1990 | Dailey et al. | 73/12.09 |
| 4,970,890 | 11/1990 | Jaafar et al. | 73/12.09 |
| 5,012,684 | 5/1991 | Humphries | 73/865.8 |
| 5,020,234 | 6/1991 | Alkire et al. | 73/865.8 |
| 5,295,388 | 3/1994 | Fischer et al. | 73/12.09 |

*Primary Examiner*—Richard Chilcot
*Assistant Examiner*—Elizabeth L. Dougherty

[57] ABSTRACT

An improved apparatus for impact testing stator wedge tightness in an electrical generator includes a base assembly that has a vibration sensor mounted thereon and is adapted to temporarily attached to a stator core lamination in an electrical generator, an impact assembly for creating an impact against the stator core lamination; and a mounting system for mounting the base assembly to the impact assembly. The mounting system includes an isolating system for vibrationally isolating the base assembly from the impact assembly during use, so that the vibration sensor will receive vibrations from the stator core lamination, and not said impact assembly. The method of use is also disclosed.

15 Claims, 3 Drawing Sheets

SYSTEM AND METHOD FOR IMPACT TESTING WEDGE TIGHTNESS IN AN ELECTRICAL GENERATOR

FIELD OF THE INVENTION

This invention relates to systems and methods for impact testing stator wedge tightness in an electrical generator that has had its rotor assembly removed.

DESCRIPTION OF THE PRIOR ART

During scheduled and forced outages of electric utility steam driven electrical generators, one of the major concerns is the condition of the stator coils. Many tests are performed to quantify stator integrity. The most time-consuming of these tests has been the test of stator wedge tightness. In the past, the standard method for testing stator wedge tightness involved having an experienced technician tap on the wedge with a small hammer, feel the wedge vibration with his or her free finger, and listen for hollow "loose" and solid "tight" sounds. He or she would then make a subjective judgement as to whether the wedge was loose, tight, or somewhere in between.

U.S. Pat. No. 4,962,660 to Dailey et al. ("Dailey") discusses an apparatus for impact testing stator wedge tightness that was developed, as this invention was, at Westinghouse Electric Corporation. Dailey describes a low-profile remotely controlled carriage that is inserted between the rotor and stator of an electric generator. The carriage carries an impactor that can be preloaded to strike the stator wedges in all orientations around the stator with a selected high impact force that causes the stator wedge to vibrate. A detector seismically senses the deflections in the vibrating stator wedge. Preferably, the detector includes an eddy current coil positioned to measure the distance to a wedge follower that vibrates with the wedge. In one embodiment, the wedge follower is a vacuum cup secured to the wedge. In another, the eddy current coil measures the distance to a foot spring biased against the vibrating wedge. Preferably, the detector is seismically isolated by mounting it on a separate carriage disposed in an aperture in a low profile carriage.

The Dailey device is effective in measuring stator wedge tightness when the rotor assembly is in place within the generator assembly. However, during major outages, the rotor assembly is likely to be removed from the generator assembly. What is required for such major outage, rotor out situations is an inexpensive, simple, reliable device to measure, quantify, and record stator wedge tightness.

SUMMARY OF THE INVENTION

Accordingly, it is an object of this invention to provide an inexpensive, simple, reliable device for measuring, quantifying, and recording stator wedge tightness for major outage, rotor out generator maintenance situations.

In order to achieve the above and other objects of the invention, an improved apparatus for impact testing stator wedge tightness in an electrical generator includes, according to a first aspect of the invention, a base assembly having a vibration sensor that is mounted thereon, the base assembly further including an attaching system for temporarily attaching the base assembly to a stator core lamination in an electrical generator; an impact assembly for creating an impact against a stator core lamination; and a mounting mechanism for mounting the base assembly to the impact assembly, the mounting mechanism including an isolating system for vibrationally isolating the base assembly from the impact assembly during use, whereby the vibration sensor will receive vibrations from the stator core lamination, and not the impact assembly.

An improved apparatus for impact testing stator wedge tightness in an electrical generator includes, according to a second aspect of the invention, a base assembly having a vibration sensor mounted thereon, the base assembly further including an attaching system for temporarily attaching the base assembly to a stator core lamination in an electrical generator; an impact assembly for impacting a stator core lamination, the impact assembly including an electrical impact drive mechanism and an impacting tool driven by the impact drive mechanism; and a mounting system for mounting the base assembly to the impact assembly.

A method of impact testing stator wedge tightness in an electrical generator includes, according to a third aspect of the invention, the steps of (a) attaching a base assembly having a vibration sensor mounted thereon to a stator core lamination in an electrical generator; (b) creating an impact against the stator core lamination with an impact assembly; and (c), simultaneously with step (b), vibrationally isolating the base assembly from the impact assembly during use, whereby the vibration sensor will receive vibrations from the stator core lamination, and not the impact assembly.

These and various other advantages and features of novelty which characterize the invention are pointed out with particularity in the claims annexed hereto and forming a part hereof. However, for abetter understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 1:
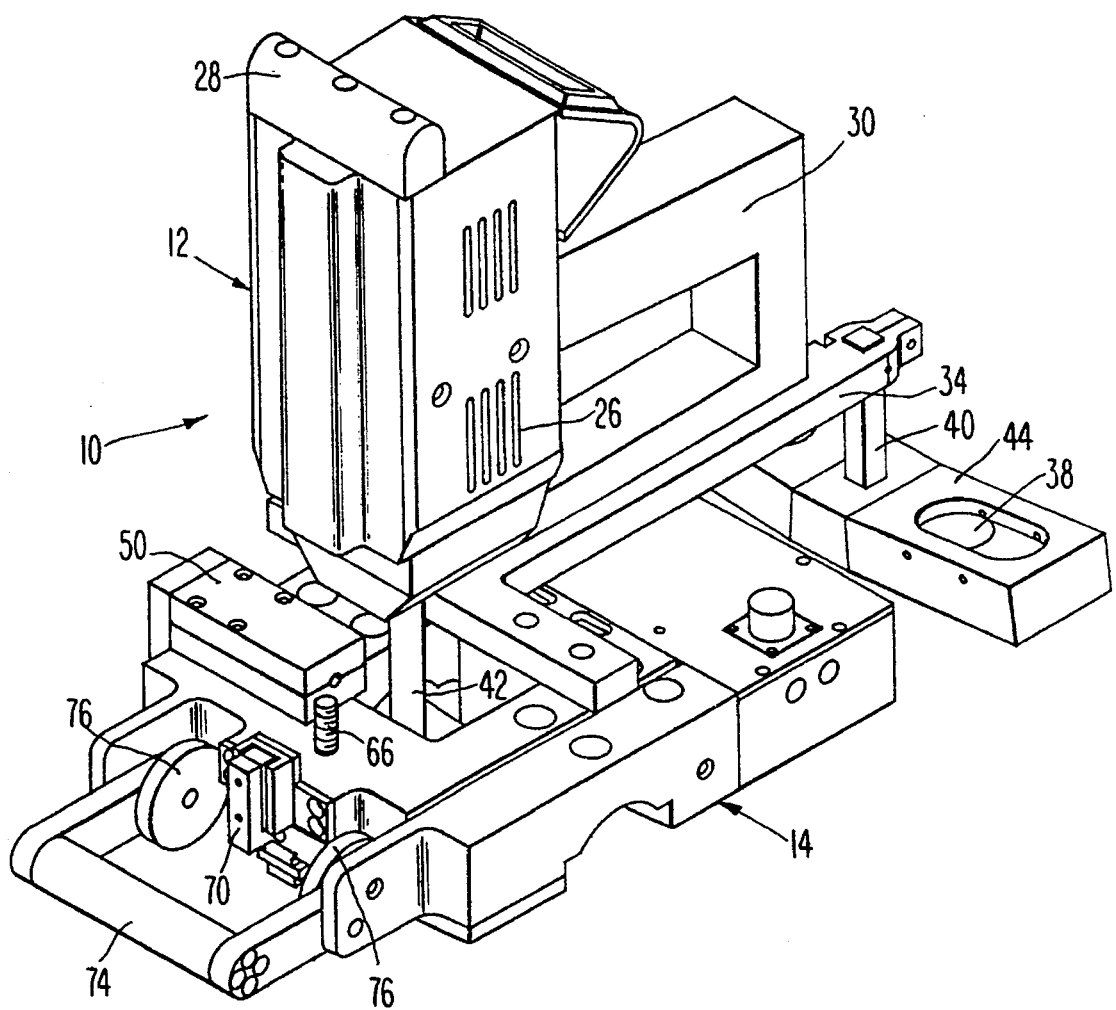
FIG. 1 is a perspective view of an apparatus for impact testing stator wedge tightness that is constructed according to a preferred embodiment of the invention.

Referring now to the drawings, wherein like reference numerals designate corresponding structure throughout the views, and referring in particular to FIG. 1, an improved apparatus 10 for impact testing stator wedge tightness in an electrical generator includes an impact assembly 12 and a base assembly 14. Base assembly 14 has a vibration sensor 16 mounted thereon, and further includes an attaching mechanism 18 for attaching the base assembly 14 to a stator core lamination in an electrical generator when the rotor assembly has been removed from the generator.

Figure 2A:
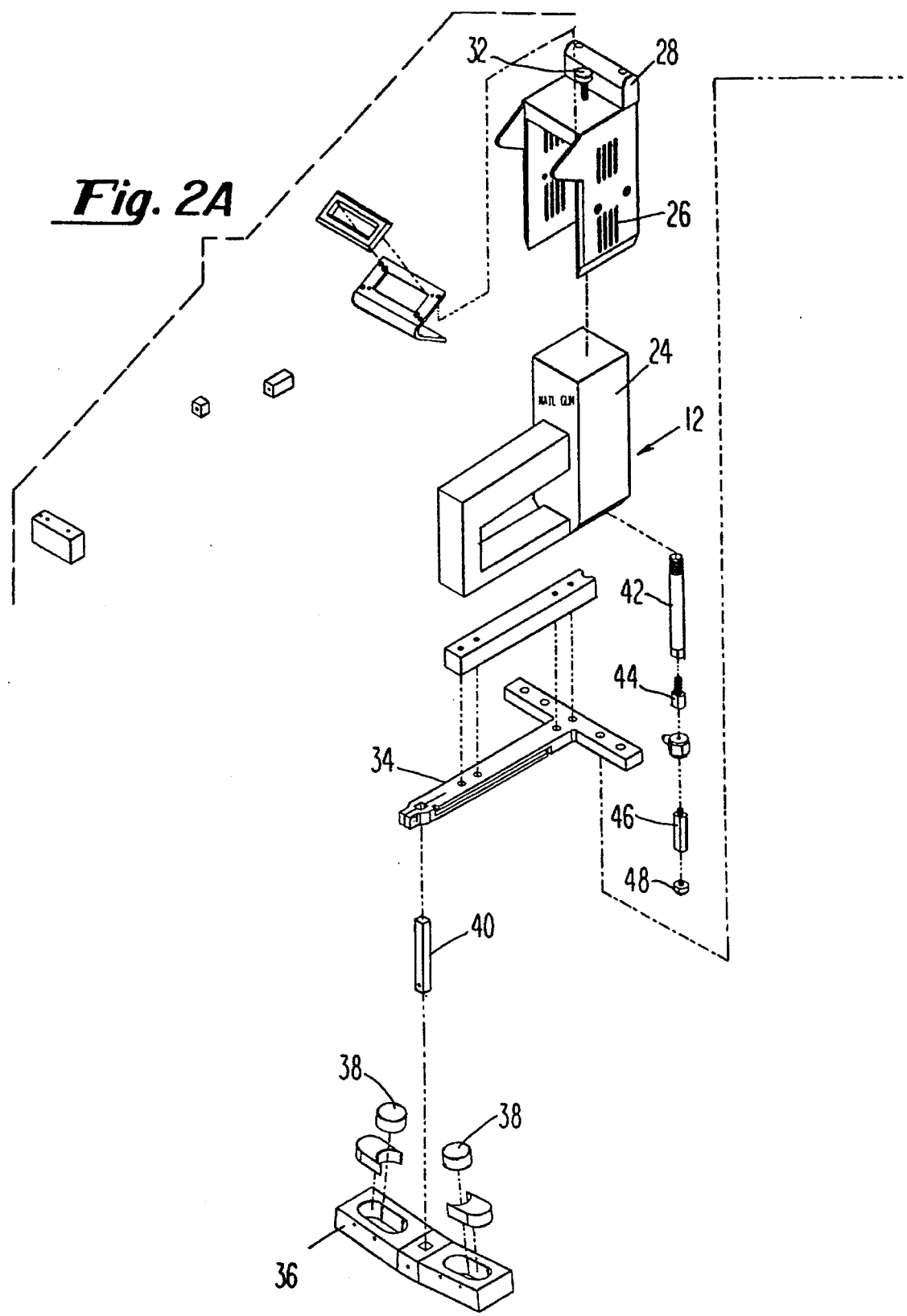
FIGS. 2A and 2B are exploded views of the apparatus that is depicted in FIG. 1.
Figure 2B:
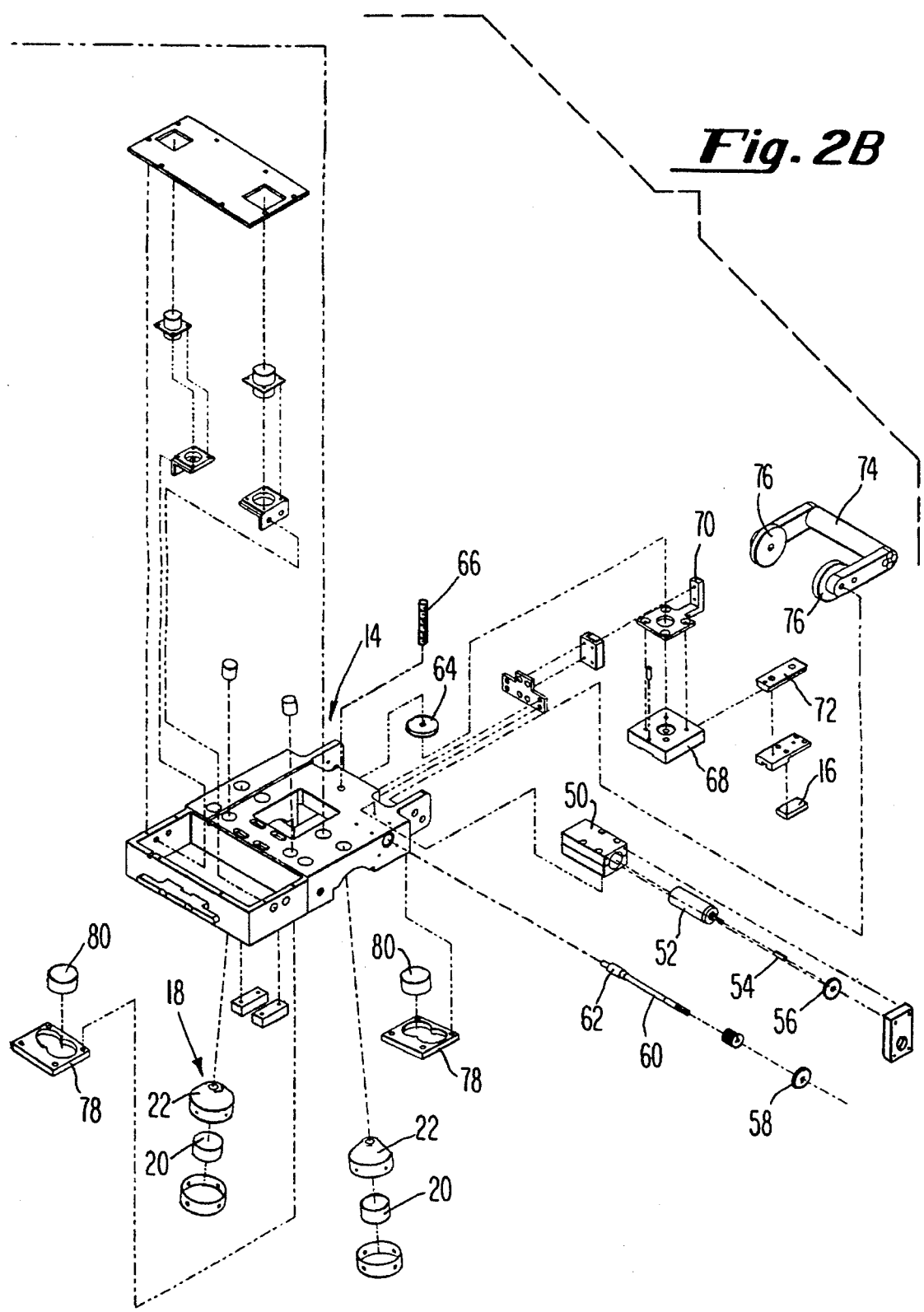

Referring now to FIG. 2B, it will be seen that the attaching mechanism 18 includes a number of magnets 20 that are mounted in elastomeric bushings 22. Bushings 22 are mounted to impact assembly 12 by a corresponding number of bolts that pass through holes that are defined in base assembly 14, as may readily be visualized from FIGS. 2A and 2B. Attaching mechanism 18 further includes a number of magnets 80 that are held in place to base assembly 14 by a corresponding number of brackets 78, as may also be seen in FIG. 2B.

Looking again to FIG. 2A, it will be seen that impact assembly 12 includes a drive mechanism 24 that is taken from an electric nail gun. A cover 26 having a handle 28 is preferably mounted to the drive mechanism 24, as may be seen FIG. 2A. Cover 26 includes a force control rod 32 for controlling the force by,which drive mechanism 24 drives an impacting tool (described hereinbelow) into the stator coil laminations. Force control rod 32 is threaded into the top of cover 26 in order to provide an adjustable starting point for the moving solenoid core within the drive mechanism 24. The higher the starting point, the greater the wedge impact force. As the threaded rod is screwed further into the cover and solenoid center, the moving solenoid core starting point is moved in the direction of the stator wedge, which reduces the peak dynamic stator wedge impact force. The position of the threaded rod and resulting maximum wedge impact force is thus adjusted during the calibration process.

According to one important aspect of the invention, the impact tool of impact assembly 12 includes a detachable adapter rod for permitting the apparatus to be used with different generator frame sizes and wedge depths. Referring to FIG. 2A, it will be seen that the impacting tool includes a first impact rod 42 that threads into the drive mechanism 24, a first adapter rod 44, a second adapter rod 46, an a stainless steel impact ball. The impact ball 48 threads into the second adapter rod 46, which in turn threads into the first adapter rod 44. The first adapter rod 44 threads into the end of first impact rod 42 that is opposite from the end that is threaded into the drive mechanism 24. By adjusting the length of the impacts rod 42 and the adapter rods 44, 46, it will be seen that the apparatus 10 will be adaptable to different types of generators. In other words, the adapter rods are made in a variety of lengths to accommodate the variation in wedge depth that occurs with different generator frame sizes and with different manufactures.

Before a stator wedge can be impacted and its vibration measured, the capacitive sensor 16 must be positioned approximately 0.025 inch above the wedge. The positioning process has to be controllable and repeatable over a wide range of possible wedge depths, which vary from machine to machine by slightly more than 1 inch. Sensor positioning is accomplished by using a preloaded ball slide, which is adjusted to remove all free play. With this arrangement, the sensor 16 can only translate up and down; skewing, cocking, or rocking motion is eliminated. Referring to FIG. 2B, capacitive sensor 16 is translated up and down on the ball slide by means of a motor 52, which is mounted to base assembly 14 by means of a bracket 50. Motor 52 turns a shaft 54, which in turn drives a gear 56 against a second gear 58. Second gear 58 drives a second shaft 60, which in turn drives a worm 62, as may readily visualized from FIG. 2B. Worm 62 engages worm gear 64, which has a threaded hole at its center. As the worm gear 64 rotates in a fixed position, threaded rod 66 moves up and down, carrying attached dovetail bracket 68 with it. Dovetail bracket 68 is bolted to stainless steel bracket 70, which attaches directly to the moving half of the ball slide. The capacitive sensor 16 is bolted to a male dovetail bracket 72, which slides into the female dovetail in bracket 68. Dovetail bracket 68 has a ball detent that causes bracket 72 to snap into position. This makes bracket 72 easy to remove, and removes all free play between brackets 68, 72.

As may further be seen in FIG. 2A and 2B, a handle 74 is pivotally mounted to one end of the base assembly 14. A pair of wheels 76 are attached to handle 74 in such a manner that wheels 76 will engage in underlying surface, such as a stator coil lamination, when the handle 74 is rotated downwardly, as shown in FIG. 2B.

In operation, the operator will position the apparatus 10 over the center of a stator coil wedge. The operator will then apply downward pressure onto the handle 28, which seats the impact assembly 12 against the underlying stator coil lamination, and seismically isolates the impact assembly 12 from the capacitive vibration pickup 16. As the solenoid core in the drive mechanism 24 travels downward, it causes the nail gun T-bracket support 34 to vibrate. The T-bracket support is supported by rod 40, and two threaded rods that are attached to rubber bushings 22 and magnets 20. In operation, bushings 22 and bracket 36 will rest directly on the stator laminations. Furthermore, when the instrument is fully seated onto the stator core, the bracket 36 and the bushings 22 are in clearance with the base assembly 14, which contains the capacitive sensor 16. Therefore, none of the vibration caused by the moving solenoid core travel through these parts and into the capacitive sensor 16. Due to the clearance and magnets holding the base assembly 14 firmly to the stator lamination, the capacitive sensor 16 remains solidly secured to the laminations during the entire wedge impact process.

When the operator moves the apparatus 10 to test another wedge, he or she will lift upward on handle 74, causing wheels 76 to rotate downwardly so that they contact the stator lamination. This pries the base assembly 14 off of the stator lamination. At the same time, the operator will use his or her other hand to lift upwardly on the impact assembly 12, thus breaking the magnetic force of attraction of the two magnets in the rubber bushings 22. With the magnetic attraction thus reduced, the operator will then slide the unit to the next wedge and the instrument will roll on the wheels 76 and slide on the back edge of the holding bracket 36. Once the instrument is positioned over the next wedge, handle 74 is rotated back to horizontal. The impact assembly 12 is pushed downwardly with the other hand, all of the magnets reattached to the stator lamination, and the critical seismic isolation clearances will return to form automatically.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An improved apparatus for impact testing stator wedge tightness in an electrical generator, comprising:

a base assembly having a vibration sensor mounted thereon, said base assembly further comprising attaching means for temporarily attaching said base assembly to a stator core lamination in an electrical generator;

an impact assembly for creating an impact against a stator core lamination; and mounting means for mounting said base assembly to said impact assembly, said mounting means including isolating means for vibrationally isolating said base assembly from said impact assembly during use, whereby said vibration sensor will receive vibrations from the stator core lamination, and not said impact assembly.

2. An apparatus according to claim 1, wherein said attaching means comprises at least one magnet.

3. An apparatus according to claim 1, wherein said impact assembly comprises a drive mechanism for an electric nail gun.

4. An apparatus according to claim 1, wherein said impact assembly comprises a handle and a trigger switch for actuating said impact assembly.

5. An apparatus according to claim 1, wherein said isolating means comprises means for permitting limited displacement to take place between said impact means and said base assembly.

6. An apparatus according to claim 1, wherein said isolating means further comprises absorbing means interposed between said impact means and said base assembly for absorbing vibrations.

7. An apparatus according to claim 6, wherein said absorbing means comprises at least one resilient bushing.

8. An improved apparatus for impact testing stator wedge tightness in an electrical generator, comprising:

a base assembly having a vibration sensor mounted thereon, said base assembly further comprising attaching means for temporarily attaching said base assembly to a stator core lamination in an electrical generator;

an impact assembly for impacting a stator core lamination, said impact assembly comprising an electrical impact drive mechanism and an impacting tool driven by said impact drive mechanism; and mounting means for mounting said base assembly to said impact assembly.

9. An apparatus according to claim 8, wherein said attaching means comprises at least one magnet.

10. An apparatus according to claim 8, wherein said impact assembly comprises a drive mechanism for an electric nail gun.

11. An apparatus according to claim 8, wherein said impact assembly comprises a handle and a trigger switch for actuating said impact assembly.

12. An apparatus according to claim 8, wherein said impacting tool comprises a detachable adapter rod for permitting said apparatus to be used with different generator frame sizes and wedge depths.

13. A method of impact testing stator wedge tightness in an electrical generator, comprising steps of:

(a) attaching a base assembly having a vibration sensor mounted thereon to a stator core lamination in an electrical generator;

(b) creating an impact against a stator core lamination with an impact assembly; and (c) simultaneously with step (b), vibrationally isolating the base assembly from the impact assembly during use, whereby said vibration sensor will receive vibrations from the stator core lamination, and not said impact assembly.

14. A method according to claim 13, further comprising the step of seating the impact assembly against the stator core lamination prior to step (b).

15. A method according to claim 13, wherein the impact assembly has a detachable impacting tool, and further comprising the step of selecting and installing an impacting tool of the proper length for the subject generator prior to step (b).

* * * * *